US008435354B2

(12) United States Patent
Noda et al.

(10) Patent No.: US 8,435,354 B2
(45) Date of Patent: *May 7, 2013

(54) WATER STABLE COMPOSITIONS AND ARTICLES COMPRISING STARCH AND METHODS OF MAKING THE SAME

(75) Inventors: Isao Noda, Fairfield, OH (US); Michael M. Satkowski, Oxford, OH (US); William M. Allen, Jr., Liberty Township, OH (US); James T. Knapmeyer, Rossmoyne, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/545,262

(22) Filed: Oct. 10, 2006

(65) Prior Publication Data

US 2007/0082981 A1 Apr. 12, 2007

Related U.S. Application Data

(60) Provisional application No. 60/725,424, filed on Oct. 11, 2005.

(51) Int. Cl.
C08B 30/12 (2006.01)
C08B 30/00 (2006.01)
C08L 3/00 (2006.01)
C08L 89/00 (2006.01)
D21H 19/54 (2006.01)
D06M 15/11 (2006.01)

(52) U.S. Cl.
USPC .................... 127/33; 127/71; 524/47; 524/53

(58) Field of Classification Search .................... 524/47, 524/53; 127/33, 71
See application file for complete search history.

(56) References Cited

U.S. PATENT DOCUMENTS

| | | | |
|---|---|---|---|
| 2,850,468 A * | 9/1958 | Giggey | 524/53 |
| 3,320,200 A * | 5/1967 | Kane | 524/89 |
| 3,417,413 A | 12/1968 | Gage | |
| 3,767,604 A * | 10/1973 | Hjermstad et al. | 24/50 |
| 3,848,594 A | 11/1974 | Buell | |
| 3,860,003 A | 1/1975 | Buell | |
| 3,985,937 A * | 10/1976 | Fife | 428/486 |
| 4,542,178 A * | 9/1985 | Zimmermann et al. | 524/388 |
| 4,589,876 A | 5/1986 | Van Tilburg | |
| 4,600,739 A * | 7/1986 | Krankkala | 524/48 |
| 4,615,739 A * | 10/1986 | Clark et al. | 106/34 |
| 4,673,438 A | 6/1987 | Wittwer et al. | |
| 4,687,478 A | 8/1987 | Van Tilburg | |
| 4,826,719 A * | 5/1989 | Murdock et al. | 428/182 |
| 5,093,393 A * | 3/1992 | Faber et al. | 524/30 |
| 5,095,054 A | 3/1992 | Lay et al. | |
| 5,106,890 A * | 4/1992 | Maruhashi et al. | 524/47 |
| 5,234,977 A | 8/1993 | Bastioli et al. | |
| 5,258,430 A | 11/1993 | Bastioli et al. | |
| 5,262,458 A | 11/1993 | Bastioli et al. | |
| 5,286,770 A | 2/1994 | Bastioli et al. | |
| 5,292,782 A | 3/1994 | Bastioli et al. | |
| 5,334,639 A * | 8/1994 | Rice | 524/47 |
| 5,382,611 A * | 1/1995 | Stepto et al. | 524/47 |
| 5,393,804 A | 2/1995 | George et al. | |
| 5,399,728 A * | 3/1995 | Cooper | 554/149 |
| 5,409,973 A | 4/1995 | Bastioli et al. | |
| 5,412,005 A | 5/1995 | Bastioli et al. | |
| 5,462,980 A | 10/1995 | Bastioli et al. | |
| 5,462,982 A * | 10/1995 | Bastioli et al. | 524/47 |
| 5,498,692 A | 3/1996 | Noda | |
| 5,512,617 A | 4/1996 | Ritter et al. | |
| 5,560,962 A * | 10/1996 | Brunger et al. | 427/475 |
| 5,716,675 A | 2/1998 | Andersen et al. | |
| 5,736,586 A | 4/1998 | Bastioli et al. | |
| 5,736,595 A * | 4/1998 | Gunther et al. | 524/45 |
| 5,776,619 A | 7/1998 | Shanton | |
| 6,096,809 A | 8/2000 | Lorcks et al. | |
| 6,231,970 B1 * | 5/2001 | Andersen et al. | 428/332 |
| 6,235,816 B1 | 5/2001 | Lorcks et al. | |
| 6,277,899 B1 | 8/2001 | Bastioli et al. | |
| 6,368,990 B1 | 4/2002 | Jennergren et al. | |
| 6,472,042 B1 | 10/2002 | Dibbern et al. | |
| 6,506,824 B1 | 1/2003 | Bastioli et al. | |
| 6,562,939 B1 | 5/2003 | Farachi et al. | |
| 6,632,862 B2 * | 10/2003 | Willett et al. | 524/13 |
| 6,699,363 B2 * | 3/2004 | Moffett | 162/168.3 |
| 6,730,724 B1 | 5/2004 | Bastioli et al. | |
| 6,797,753 B2 * | 9/2004 | Benecke et al. | 524/114 |

(Continued)

FOREIGN PATENT DOCUMENTS

DE 2708513 A1 8/1978
EP 0 696 612 A2 2/1996

(Continued)

OTHER PUBLICATIONS

Xanthos, M and Todd, D.B., Plastics Processing, 2004, John Wiley and Sons Inc.*
Zamora, Fatty Oils, Fatty Acids and Triglycerides, 2005, http://www.scientificpsychic.com/fitness/fattyacids1.html.*
PCT International Search Report dated Feb. 16, 2007, 3 pages.
U.S. Appl. No. 11/545,264, filed Oct. 10, 2006, Noda et al.
U.S. Appl. No. 11/545,265, filed Oct. 10, 2006, Noda et al.
U.S. Appl. No. 11/545,263, filed Oct. 10, 2006, Noda et al.
Martin, Olivier, et al., "Properties of biodegradable multilayer films based on plasticized wheat starch", Starch, 2001, 53(8), 372-380.
Shogren, R.L., et al., "Biodegradable laminates and composites containing starch and poly(hydroxyesterethers)", Annual Technical Conference—Society of Plastics Engineers, 2000, 58th (vol. 3), 3792-3795.

(Continued)

Primary Examiner — Liam Heincer
(74) Attorney, Agent, or Firm — Melody A. Jones

(57) ABSTRACT

Thermoplastic polymer compositions comprising starch and articles made therefrom are water stable or may be rendered so. One method of making water stable thermoplastic compositions comprises the steps of mixing destructured starch with polyhydric alcohol and triglyceride, and forming a transesterification reaction product from at least a portion of the polyhydric alcohol and triglyceride.

18 Claims, No Drawings

U.S. PATENT DOCUMENTS

| | | | |
|---|---|---|---|
| 7,077,994 B2 | 7/2006 | Bond et al. | |
| 7,098,292 B2 | 8/2006 | Zhao et al. | |
| 2001/0039303 A1* | 11/2001 | Loercks et al. | 524/47 |
| 2002/0013252 A1* | 1/2002 | Schmiedel et al. | 510/446 |
| 2002/0188041 A1 | 12/2002 | Bond et al. | |
| 2003/0109605 A1 | 6/2003 | Bond et al. | |
| 2003/0119949 A1* | 6/2003 | Favis et al. | 524/47 |
| 2003/0129348 A1* | 7/2003 | Peng | 428/41.8 |
| 2003/0207038 A1* | 11/2003 | Han et al. | 427/384 |
| 2003/0216492 A1* | 11/2003 | Bowden et al. | 524/47 |
| 2003/0219516 A1 | 11/2003 | Pater et al. | |
| 2004/0014844 A1* | 1/2004 | Helbling et al. | 524/47 |
| 2004/0096656 A1 | 5/2004 | Bond | |
| 2004/0140055 A1* | 7/2004 | Chen et al. | 156/355 |
| 2004/0197554 A1 | 10/2004 | Bond et al. | |
| 2004/0209980 A1* | 10/2004 | Patrone et al. | 524/35 |
| 2004/0249021 A1* | 12/2004 | Hwang et al. | 523/200 |
| 2005/0020472 A1* | 1/2005 | Kottwitz et al. | 510/473 |
| 2005/0026529 A1 | 2/2005 | Bond et al. | |
| 2005/0029703 A1 | 2/2005 | Franke et al. | |
| 2005/0076809 A1* | 4/2005 | Mackey et al. | 106/206.1 |
| 2005/0107603 A1 | 5/2005 | Peltonen et al. | |
| 2005/0169983 A1 | 8/2005 | Hassan et al. | |
| 2005/0176326 A1 | 8/2005 | Bond et al. | |
| 2005/0182196 A1 | 8/2005 | Khemani et al. | |
| 2005/0205574 A1* | 9/2005 | Lambotte et al. | 220/234 |
| 2006/0141592 A1* | 6/2006 | Sumida et al. | 435/134 |
| 2006/0148943 A1* | 7/2006 | Mikkonen et al. | 524/112 |
| 2006/0160937 A1* | 7/2006 | Hecaen et al. | 524/391 |
| 2006/0199881 A1 | 9/2006 | Xu | |
| 2006/0252855 A1* | 11/2006 | Pisanova et al. | 524/47 |
| 2006/0264539 A1* | 11/2006 | Mosseveld et al. | 524/47 |
| 2006/0276575 A1* | 12/2006 | Hamaguchi et al. | 524/308 |

FOREIGN PATENT DOCUMENTS

| | | |
|---|---|---|
| EP | 0 758 669 B1 | 9/2001 |
| JP | 62091502 | 4/1987 |
| JP | 09 255 880 | 9/1997 |
| JP | 2003-138063 A2 | 5/2003 |
| JP | 2005-041129 A2 | 2/2005 |
| WO | WO 93/07213 A1 | 4/1993 |
| WO | WO 93/20140 A1 | 10/1993 |
| WO | WO 93/20141 A1 | 10/1993 |
| WO | WO 98/20073 A2 | 5/1998 |

OTHER PUBLICATIONS

Huang, H.C., et al., "Mechanical and physical properties of protein-starch based plastics produced by extrusion and injection molding", Journal of the American Oil Chemists' Society, 1999, 76(9), 1101-1108.

Garcia, Maria A., et al., "Plasticized Starch-Based Coatings to Improve Strawberry (*Fragaria+ananassa*) Quality and Stability", Journal of Agricultural and Food Chemistry, 1998, 46(9), 3758-3767.

* cited by examiner

WATER STABLE COMPOSITIONS AND ARTICLES COMPRISING STARCH AND METHODS OF MAKING THE SAME

CROSS REFERENCE TO RELATED APPLICATION

This application claims the benefit of U.S. Provisional Application No. 60/725,424, filed 11 Oct. 2005.

FIELD OF THE INVENTION

The present invention relates to thermoplastic polymer compositions comprising starch and articles made therefrom. The compositions and articles are water stable, or may be rendered so. The invention also relates to methods of making the water stable thermoplastic polymer compositions and articles.

BACKGROUND OF THE INVENTION

Thermoplastic polymers find use in a variety of plastic articles including, but not limited to films, sheets, adhesives, binders, laminates, coatings, fibers, foams, molded articles, and the like. Often, the plastic articles have a short use cycle, as in the areas of packaging, agriculture, household goods, and personal care products. For example, in the packaging of food, plastic articles often play the role of a protective agent and are quickly disposed of after the food is consumed. Likewise, plastic household articles such as detergent bottles, and plastic personal care products such as diapers and tampon applicators, are discarded upon use.

Typically, plastic articles are made from petroleum-based thermoplastic polymers including, but not limited to, polyolefins. However, the use of petroleum-based thermoplastic polymers is becoming less pragmatic due to disruptions in petroleum supply and increasing expense. Additionally, after use it is common for petroleum-based plastic materials, which are typically not biodegradable, to become solid waste that is to be discarded in rapidly vanishing, increasingly expensive landfill space.

Thermoplastic starch (TPS) has been identified as a substitute for petroleum-based polymers. The use of TPS is advantageous since starch is naturally abundant, and relatively inexpensive. Moreover, TPS has desirable properties not typically observed in conventional petroleum-based polymers including, but not limited to, biodegradability, natural hydrophilicity and compatibility with materials traditionally incompatible with petroleum-based polymers.

To render starch thermoplastic for processing, it is typically combined with one or more plasticizers and/or other processing aids. Like many petroleum-based polymers, TPS may be processed using conventional means including, but not limited to, melt spinning and other melt extrusion techniques. However, unlike many petroleum-based polymers, TPS is susceptible to moisture. When exposed to water, TPS can partially or even fully disintegrate within hours. This susceptibility to moisture can limit the applications in which TPS may be utilized. One proposed solution to overcome the susceptibility of TPS to water is to blend it with petroleum-based polymers including, but not limited to, polyolefins. However, the addition of petroleum-based polymers to TPS may propagate disadvantages such as those described above.

There remains a need for water stable thermoplastic polymer compositions made from abundant, low-cost starch. The thermoplastic polymer compositions would advantageously be water stable without requiring the use of additives including, but not limited to, petroleum products and the like.

A further need remains for water stable plastic articles comprising TPS compositions, which may optionally be biodegradable. It would also be advantageous for such articles to be water stable without requiring the use of additives including, but not limited to, petroleum based products and the like.

It is also desirable to provide starch compositions that may be converted into water stable thermoplastic polymer compositions. Plastic articles made from such compositions could be rendered water stable during or after processing. Additionally, it is desirable to provide the starch compositions, and/or components thereof, in forms that are easy to make, ship, process, and combinations thereof.

SUMMARY OF THE INVENTION

In some embodiments, the present invention relates to water stable thermoplastic polymer compositions comprising destructured starch, and transesterification reaction products formed from a reaction mixture comprising polyhydric alcohol and triglyceride. In some embodiments, the composition comprises destructured starch and reaction products of polyhydric alcohol and a compound, wherein the reaction products are transesterification reaction products, ester condensation reaction products, and combinations thereof.

Plastic articles that may be made from the disclosed water stable thermoplastic polymer compositions include, but are not limited to molded articles, extruded articles, and combinations thereof. Specific embodiments include personal hygiene articles, absorbent articles, and packaging.

In some embodiments, the present invention relates to starch compositions which may be converted to water stable thermoplastic polymer compositions. These compositions comprise starch (which is destructured before addition to the composition and/or in situ), polyhydric alcohol, triglyceride and optionally acid. Methods are disclosed by which the starch compositions may be rendered water stable; the method steps may be performed in any suitable order. The methods include inducing transesterification reactions between polyhydric alcohol and triglyceride and/or inducing ester condensation reactions between the polyhydric alcohol and acid. In some embodiments, the reaction(s) are induced through the addition of heat.

These and other embodiments, aspects, and advantages are encompassed within the present invention, and will become better understood with regard to the following description and appended claims.

DETAILED DESCRIPTION OF THE INVENTION

All percentages, ratios and proportions used herein are by weight percent of the composition, unless otherwise specified. All average values are calculated "by weight" of the composition or components thereof, unless otherwise expressly indicated. "Average molecular weight," or "molecular weight" for polymers, unless otherwise indicated, refers to weight average molecular weight. Weight average molecular weight, unless otherwise specified, is determined by gel permeation chromatography.

"Copolymer" as used herein is meant to encompass copolymers, terpolymers, and other multiple-monomer polymers.

"Reactant" as used herein refers to a chemical substance that is present at the start of a chemical reaction.

"Mixture" as used herein refers to a mixture of two or more of any of a defined group of components, unless otherwise specified.

"Biodegradable" as used herein refers to the ability of a compound to ultimately be degraded completely into $CH_4$, $CO_2$ and water or biomass by microorganisms and/or natural environmental factors.

"Compostable" as used herein refers to a material that meets the following three requirements: (1) the material is capable of being processed in a composting facility for solid waste; (2) if so processed, the material will end up in the final compost; and (3) if the compost is used in the soil, the material will ultimately biodegrade in the soil.

"Comprising" as used herein means that various components, ingredients or steps can be conjointly employed in practicing the present invention. Accordingly, the term "comprising" encompasses the more restrictive terms "consisting essentially of" and "consisting of". The present compositions can comprise, consist essentially of, or consist of any of the required and optional elements disclosed herein.

Markush language as used herein encompasses combinations of the individual Markush group members, unless otherwise indicated.

All percentages, ratios and proportions used herein are by weight percent of the composition, unless otherwise specified. All average values are calculated "by weight" of the composition or components thereof, unless otherwise expressly indicated.

All numerical ranges disclosed herein, are meant to encompass each individual number within the range and to encompass any combination of the disclosed upper and lower limits of the ranges.

The present invention is directed to starch compositions, as well as thermoplastic polymer compositions comprising starch and plastic articles made therefrom, which are, or may be rendered, water stable. The present invention is also directed to methods of making the same.

The water stable thermoplastic polymer compositions of the present invention are made from mixtures of materials also referred to herein as "starch compositions". The starch compositions may comprise: destructured starch; polyhydric alcohol; and triglyceride and/or acid (comprising carboxylic acid, and/or carboxylic acid anhydride moieties), and the like. Without wishing to be bound by theory, it is believed that the polyhydric alcohol acts as a plasticizer which makes destructured starch thermoplastic and capable of being processed via methods including, but not limited to, those that are used for processing conventional thermoplastics. It is further believed that by heating the mixture of materials, a transesterification reaction is induced between at least a portion of the polyhydric alcohol and the triglyceride, and/or an ester condensation reaction is induced between at least a portion of the polyhydric alcohol and acid. It is believed that these reactions, either alone or in combination, make at least a portion of the polyhydric alcohol water insoluble. It is believed that the water insoluble polyhydric alcohol may provide the resulting thermoplastic polymer compositions (or articles made therefrom) with "water stability". "Water stability" generally refers to the ability to withstand moisture and is measured as specified in the Methods section below. Thus, thermoplastic compositions comprising starch of the present invention may be water stable without requiring the use of petroleum based polymers and the like.

In some embodiments, the polyhydric alcohol and the triglyceride and/or acid may be present in the starch compositions as what is termed herein as a "pre-polymer". In these instances, the aforementioned transesterification reaction and/or ester condensation reaction has already at least partially, but not completely, taken place between the polyhydric alcohol and the triglyceride and/or acid before it is mixed with the starch. In further embodiments, the pre-polymer may also contain starch.

The aforementioned materials, articles and methods of making the same are further discussed below.

Starch

Starch is naturally abundant and can be relatively inexpensive. Thermoplastic starch can have desirable properties not typically observed in conventional petroleum-based polymers including, but not limited to, biodegradability, compostability, natural hydrophilicity and compatibility with materials traditionally incompatible with petroleum-based polymers.

Starch may take several different forms. As used herein, "native starch" means starch as it is found in its naturally occurring, unmodified form. Any suitable source of native starch is of use in the present invention. Non-limiting examples of sources include: corn starch, potato starch, sweet potato starch, wheat starch, sago palm starch, tapioca starch, rice starch, soybean starch, arrow root starch, bracken starch, lotus starch, cassava starch, waxy maize starch, high amylase corn starch, commercial amylase powder, and combinations thereof.

Native starch generally has a granular structure. In order to render starch capable of further processing, it is typically subject to a destructuring process. Without wishing to be bound by theory, it is believed that a starch granule is comprised of discrete amylopectin and amylase regions. To convert native starch to "destructured starch", the regions are broken apart during the destructurization process, which is often followed by a volume expansion of the starch, particularly in the presence of additives including, but not limited to, plasticizer. The presence of a plasticizer, such as polyhydric alcohol, when starch is destructured typically increases the starch's viscosity as compared to starch that is destructured in its absence. The destructuring process is typically irreversible. In some embodiments of the present invention, it may be desirable to destructure the starch as fully as possible, so as to avoid "lumps" which may have an adverse impact in subsequent processing steps including, but not limited to melt processing.

Native starch of use in the present invention may be destructured prior to its inclusion in the mixtures of present invention. In addition, or in the alternative, native starch may be destructured after it is in the mixture, i.e., in situ. In some embodiments of the present invention, the use of native starch is less expensive than using destructured starch, as it eliminates the use of a separate, destructuring step.

Native starch may be destructured using any suitable means. At least partial destructuring may be achieved through means including, but not limited to: heating; enzyme modification; chemical modification including but not limited to ethoxylation and the like (such as by adding ethylene oxide for example); chemical degradation; and combinations thereof. Agents that may act as starch plasticizers may be used to destructure the starch. In some embodiments, these agents may remain mixed with the starch during further processing. In other embodiments, the agents may be transient, meaning that they are removed so that they are not present during further processing, and/or in the final plastic article.

In some embodiments, destructured starch may encompass native starch that has been destructured by modification, as discussed above. Modified starch is defined as a native starch that has had its native molecular characteristics (molecular weight or chemical structure) altered in any way. For example, in some embodiments, if the molecular weight of the native starch is changed, but no other changes are made to the native starch, then the starch can be referred to as a modified starch. Chemical modifications of starch typically include acid or alkali hydrolysis and oxidative chain scission to reduce molecular weight and molecular weight distribution. Native starch generally has a very high average molecular weight and a broad molecular weight distribution (e.g. native corn starch has an average molecular weight of up to about 60,000,000 grams/mole (g/mol)). The average molecular weight of starch can be reduced as desired for the present invention by acid reduction, oxidation reduction, enzymatic reduction, hydrolysis (acid or alkaline catalyzed), physical/mechanical degradation (e.g., via the thermomechanical energy input of the processing equipment), and combinations thereof. The thermomechanical method and the oxidation method offer an additional advantage when carried out in situ. The exact chemical nature of the starch and molecular weight reduction method is not critical as long as the average molecular weight is in an acceptable range. Ranges of weight average molecular weight for starch or starch blends added to the melt can be from about 3,000 g/mol to about 8,000,000 g/mol, from about 10,000 g/mol to about 5,000,000 g/mol, or from about 20,000 g/mol to about 3,000,000 g/mol. In other embodiments, the weight average molecular weight is otherwise within the above ranges but about 1,000,000 or less, or about 700,000 or less. Starches having different molecular weights may be mixed as desired for use in the invention.

In some embodiments, destructured starch encompasses substituted starch. Substituted starches are starches that have some of their alcohol (i.e., hydroxyl) functional groups replaced by other chemical moieties. If substituted starch is desired, chemical modifications of starch typically include etherification and esterification. Chemical modification can be accomplished using ethylene oxide, otherwise known as ethoxylation, resulting in destructured starch as discussed above. Substituted starches may be desired for better compatibility or miscibility with the thermoplastic polymer and polyhydric alcohol. However, it may be desirable to balance substitution with the reduction in the rate of degradability. The degree of substitution of the chemically substituted starch is typically from about 1% to about 100% (i.e., completely substituted). Alternatively, a low degree of substitution, from about 1% to about 6%, may be used.

In some embodiments, the starch compositions or the thermoplastic compositions of the present invention comprise from about 1% to about 99%, from about 30% to about 90%, from about 50% to about 85%, or from about 55% to 80% of starch, including the bound water content of the starch. The starch is selected from the group consisting of native starch, destructured starch (which may include modified starch and/or substituted starch) and combinations thereof. The term "bound water" refers to the water found naturally occurring in starch before it is mixed with other components to make the composition. In contrast, the term "free water" refers to water that may be added to a composition of the present invention. For example, free water may be incorporated as or with a plasticizer. A person of ordinary skill in the art will recognize that once the components are mixed in a composition, water can no longer be distinguished by its origin. Starch that has not been subjected to drying processes typically has bound water content under ambient conditions of about 5% to about 16% by weight of starch. In some embodiments of the present invention, the compositions and products of the invention comprise at least about 50% destructured starch, or at least about 60% destructured starch.

Starch of use in the present invention may comprise any combination of starches as described generally or specifically herein, or as known in the art. Suitable starches of use may be selected from the group consisting of: cold water insoluble starch; cold water soluble starch; and combinations thereof. Wherein "cold water" refers to water that is at or below 25° C. As used herein, cold water insoluble starch is starch that dissolves less than 25% in water at 25° C.

Thermoplastic starch used herein refers to a starch composition that is capable of flowing when at an elevated temperature (significantly above normal ambient temperature; generally above 80° C.), to the extent that the starch, or a composition comprising the starch, can be shaped into plastic articles. The plastic articles are capable of solidifying after the elevated temperature is lowered to ambient temperatures to retain the shaped form.

Polyhydric Alcohol

"Polyhydric alcohol" as used herein refers to an alcohol having two or more alcohol (i.e., hydroxyl) functional groups. Without wishing to be bound by theory, it is believed (as mentioned above) that polyhydric alcohol may act as a starch plasticizer in the starch compositions of the present invention. In other words, polyhydric alcohol is believed to enable the starch to flow and to be processed, i.e., to create a thermoplastic starch.

Any suitable polyhydric alcohol or combination of polyhydric alcohols is of use. Non-limiting examples of suitable polyhydric alcohols include: glycerol (also known in the art as glycerin), glycol, sugar, sugar alcohol, and combinations thereof. Non-limiting examples of glycols of use include: ethylene glycol, propylene glycol, dipropylene glycol, butylene glycol, hexane triol, and the like, polymers thereof, and combinations thereof. Non-limiting examples of sugars of use include: glucose, sucrose, fructose, raffinose, maltodextrose, galactose, xylose, maltose, lactose, mannose, erythrose, pentaerythritol, and mixtures thereof. Non-limiting examples of sugar alcohols of use include: erythritol, xylitol, malitol, mannitol, sorbitol, and mixtures thereof. In specific embodiments of the present invention, the polyhydric alcohol comprises glycerol, mannitol, sorbitol, and combinations thereof.

In general, the polyhydric alcohol is substantially compatible with the polymeric components with which it is intermixed. As used herein, the term "substantially compatible" means that when heated to a temperature above the softening and/or the melting temperature of the composition, the polyhydric alcohol is capable of forming a visually homogeneous mixture with polymer present in the component in which it is intermixed. In some embodiments, the plasticizer is water soluble.

In some embodiments of the present invention, the polyhydric alcohol may also be used as a destructuring agent for starch. In these embodiments, upon destructuring the starch, the polyhydric alcohol may act as a plasticizer to the destructured starch, thereby rendering it thermoplastic. In further embodiments, upon destructuring the starch, the polyhydric alcohol may be removed and substituted with a different plasticizer to render the destructured starch thermoplastic. In some embodiments, the polyhydric alcohol may improve the flexibility of the resulting plastic articles.

Polyhydric alcohol is included in the present thermoplastic compositions in any suitable amount for either destructuring starch and/or rendering destructured starch thermoplastic. Generally, the amount of polyhydric alcohol needed is dependent upon the molecular weight of the starch, the amount of starch in the mixture, the affinity of the polyhydric alcohol for the starch, and combinations thereof. The polyhydric alcohol should sufficiently render the starch component thermoplastic so that it can be processed effectively, for example to form plastic articles. Generally, the amount of polyhydric alcohol increases with increasing molecular weight of starch. Typically, the polyhydric alcohol can be present in compositions of the present invention in an amount of from about 2% to about 70%, from about 5% to about 50%, from about 10% to 30%, or from about 15% to about 25%.

Acid

Acids of use in the present invention have at least one functional group selected from the group consisting of: carboxylic acid, carboxylic acid anhydride, and combinations thereof. Such acids include, but are not limited to, monoacids, diacids, polyacids (acids having at least three acid groups), polymers comprising at least one acid moiety, co-polymers comprising at least one acid moiety, anhydrides thereof, and mixtures thereof.

Non-limiting examples of acids of use include: adipic acid, sebatic acid, lauric acid, stearic acid, myristic acid, palmitic acid, oleic acid, linoleic acid, sebacic acid, citric acid, oxalic acid, malonic acid, succinic acid, glutaric acid, maleic acid, fumaric acid, phthalic acid, isophthalic acid, terphthalic acid, acrylic acid, methacrylic acid, itaconic acid, glycidyl methacrylate, and combinations thereof. Anhydrides of such acids may also be employed within the context of the present invention. Non-limiting examples of acid anhydrides of use include: maleic anhydride, phthalic anhydride, succinic anhydride and combinations thereof.

Polymers and co-polymers comprising at least one acid moiety, and/or their anhydrides are of use. Suitable polymers and copolymers include, but are not limited to, those comprising monomer units of acrylic acid, methacrylic acid, itaconic acid, glycidyl methacrylate, anhydrides thereof, and combinations thereof. The polymer can contain other monomer units in conjunction with these acid monomer units. For example, ethylene-acid monomer copolymers such as ethylene-acrylic acid copolymer can be used. In a specific embodiment, the copolymers comprise at least 50 mol % of acid monomer units. The molecular weight of such polymers and copolymers can vary from as low as about 2,000 to over about 1,000,000. An example of a suitable polyacrylic acid is from Aldrich Chemical Company, having a molecular weight of about 450,000. An example of a suitable ethylene-acrylic acid copolymer is Primacore 59801 from Dow Chemical, having an acrylic acid content of at least 50 mol %.

In specific embodiments, the acid comprises at least one diacid, polyacid, acid polymer or copolymer, or a mixture thereof. In other embodiments, the acid comprises a diacid, alone or in combination with another acid, for example a monoacid. In further embodiments, the acid comprises adipic acid, stearic acid, lauric acid, citric acid, polyacrylic acid and/or ethylene-acrylic acid copolymer.

Typically, the acid is employed in the starch composition in an amount of from about 0.1% to about 30%, from about 1% to about 20%, or from about 2% to about 12%. In some embodiments, the molar ratio of alcohol functional groups to acidic functional groups in the starch composition is at least about 1:1, or at least about 4:1. In some embodiments, the molar ratio of alcohol functional groups to acidic groups in the starch composition is from about 1:1 to about 200:1, or from about 1:1 to about 50:1.

Triglyceride

Any suitable triglycerides, which are also known in the art as triacylglycerols, are of use in the present invention. Non-limiting examples of triglycerides of use include: tristearin, triolein, tripalmitin, 1,2-dipalmitoolein, 1,3-dipalmitoolein, 1-palmito-3-stearo-2-olein, 1-palmito-2-stearo-3-olein, 2-palmito-1-stearo-3-olein, trilinolein, 1,2-dipalmitolinolein, 1-palmito-dilinolein, 1-stearo-dilinolein, 1,2-diacetopalmitin, 1,2-distearo-olein, 1,3-distearo-olein, trimyristin, trilaurin and combinations thereof.

Suitable triglycerides may be added to the present compositions in neat form. Additionally, or alternatively, oils and/or processed oils containing suitable triglycerides may be added to the compositions. Non-limiting examples of oils include coconut oil, corn germ oil, olive oil, palm seed oil, cottonseed oil, palm oil, rapeseed oil, sunflower oil, whale oil, soybean oil, peanut oil, linseed oil, tall oil, and combinations thereof.

Typically, triglycerides are employed in the starch compositions in an amount of from about 0.1% to about 30%, from about 1% to about 20%, or from about 2% to about 12%. In some embodiments, the molar ratio of alcohol functional groups to ester functional groups in the starch composition is at least about 1:1, or at least about 4:1. In some embodiments, the molar ratio of alcohol functional groups to ester functional groups in the starch composition is from about 1:1 to about 200:1, or from about 1:1 to about 50:1.

In some embodiments, combinations of acid and triglyceride are employed in the starch compositions. In some embodiments, the total amounts of acid and triglyceride is from about 0.1% to about 32%, from about 1% to about 25%, or from about 2% to about 20%. Additionally, or alternatively, the molar ratio of the alcohol functional groups to the total of ester and acid functional groups is at least about 1:1, or at least about 4:1. In some embodiments, the molar is from about 1:1 to about 200:1, or from about 1:1 to about 50:1.

Additional Components

The compositions according to the present invention may include one or more additional components as desired for the processing and/or end use of the composition. Additional components may be present in any suitable amount. In some embodiments, additional components may be present in an amount of from about 0.01% to about 35% or from about 2% to about 20%. Non-limiting examples of additional components include, but are not limited to, additional polymers, fillers, processing aids and the like.

Non-limiting examples of additional polymers of use include: polyhydroxyalkanoates, polyvinyl alcohol, polyethylene, polypropylene, polyethylene terephthalate, maleated polyethylene, maleated polypropylene, polylactic acid, modified polypropylene, nylon, caprolactone, and combinations thereof.

In embodiments in which properties including, but not limited to, biodegradability and/or flushability are desired, additional suitable biodegradable polymers and combinations of thereof are of use. In some embodiments, polyesters containing aliphatic components are suitable biodegradable thermoplastic polymers. In some embodiments, among the polyesters, ester polycondensates containing aliphatic constituents and poly(hydroxycarboxylic) acid are preferred. The ester polycondensates include, but are not limited to: diacids/diol aliphatic polyesters such as polybutylene succinate, and polybutylene succinate co-adipate; aliphatic/aromatic polyesters such as terpolymers made of butylenes diol, adipic acid, and terephthalic acid. The poly(hydroxycarboxylic) acids include, but are not limited to: lactic acid based homopolymers and copolymers; polyhydroxybutyrate; and other polyhydroxyalkanoate homopolymers and copolymers. In some embodiments, a homopolymer or copolymer of poly lactic acid is preferred. Modified polylactic acid and different stereo configurations thereof may also be used. Suitable polylactic acids typically have a molecular weight range of from about 4,000 g/mol to about 400,000 g/mol. Examples of a suitable commercially available poly lactic acids include NATUREWORKS™ from Cargill Dow and LACEA™ from Mitsui Chemical. An example of a suitable commercially available diacid/diol aliphatic polyester is the polybutylene succinate/adipate copolymers sold as BIONOLLE™ 1000 and BIONOLLE™ 3000 from the Showa Highpolmer Company, Ltd. Located in Tokyo, Japan. An example of a suitable commercially available aliphatic/aromatic copolyester is the poly(tetramethylene adipate-co-terephthalate) sold as EASTAR BIO™ Copolyester from Eastman Chemical or ECOFLEX™ from BASF. In some embodiments, the biodegradable polymer or combination of polymers may comprise polyvinyl alcohol.

The aforementioned biodegradable polymers and combinations thereof may be present in an amount of from about 0.1% to about 70%%, from about 1% to about 50%, or from about 2% to about 25%, by weight of the present starch and thermoplastic starch compositions. Non-limiting examples of fillers include: talc, clay, pulp; flour, walnut shells, cellulose, cotton, jute, raffia, rice chaff, animal bristles, chitin, granular starch, diatomaceous earth, nanoparticles, carbon fibers, kenaf, and combinations thereof.

Processing aids are generally present in the current compositions in amounts of from about 0.1% to about 3%, or from about 0.2% to about 2%. Non-limiting examples of processing aids include: lubricants, anti-tack, polymers, surfactants, oils, slip agents, and combinations thereof. Non-limiting examples of specific processing aids include: Magnesium stearate; fatty acid amides; metal salts of fatty acids; wax acid esters and their soaps; montan wax acids, esters and their soaps; polyolefin waxes; non polar polyolefin waxes; natural and synthetic paraffin waxes; fluoro polymers; talc; silicon; clay; diatomaceous earth. Commercial examples of such compounds include, but are not limited to: Crodamide™ (Croda, North Humberside, UK), Atmer™ (Uniqema, Everberg, Belgium,) and Epostan™ (Nippon Shokobai, Tokyo, JP). In some embodiments, the starch comprises at least about 50% of all polymer components in the starch compositions, more specifically at least about 60% of all polymer components in the starch compositions.

Water Stability

Without wishing to be bound by theory, the thermoplastic polymer compositions according to the present invention may be rendered water stable via the aforementioned transesterification reaction and/or ester condensation reaction. When the thermoplastic polymer compositions are made into plastic articles, the reactions may be induced before formation of the article, during formation of the article, after the article's formation (i.e., curing) and combinations thereof. In some embodiments, the reaction(s) are induced, and/or driven towards completion through the application of heat. In some embodiments of the present invention, a catalyst may be used to initiate and/or accelerate the transesterification and/or ester condensation reactions. Any suitable catalyst is of use. Non-limiting examples of useful catalysts include Lewis acids. A non-limiting example of a Lewis acid is para-toluene sulfonic acid.

With regard to the ester condensation reaction, it is believed without being bound by theory that the heating of the thermoplastic polymer composition comprising acid, may remove a sufficient amount of water from the starch composition, (including some, but not all of the bound water) to induce a reaction of the polyhydric alcohol and the acid to form a water stable reaction product to an extent that provides the resulting composition with water stability. While again not wishing to be bound by theory, it is believed that a condensation reaction may occur between the polyhydric alcohol and acid. Generally, the chemistry which governs such condensation reactions is known in the art as alkyd chemistry.

In the present invention, it may be important that the ester condensation reaction is not completed to such an extent that a gel of the reaction products is formed before final processing of the thermoplastic composition occurs. As used herein "gel" means a material that is crosslinked to an extent that flow even under high temperatures is no longer possible without degradation of the material's molecular weight. It is important for the system to be below the gel point of the reactants before final processing so as to retain sufficient flow behavior to enable shaping of the material into plastic articles, including but not limited to fibers. The gel point is defined as the state at which enough polymer chains formed by the products of the reactants are bonded together such that at least one very large molecule is coextensive with the polymer phase and flow is no longer possible and the material behaves more like a solid.

Up until to the gel point, it may be advantageous for the reaction to proceed to a point where prepolymers such as oligomers or even larger molecules are formed, yet these species should retain the ability to flow and be shaped into useful articles. Oligomers as used herein are reaction products from constituent monomers that include at least two monomers and up to about ten monomers. In some embodiments of the current invention, when carrying out the ester condensation reaction between the acid and alcohol and thereby forming oligomers, it may be advantageous to remove excess water from the reaction product before forming the end product. It is believed that removal of the water may speed the ester condensation reaction toward completion in the final processing step.

In some embodiments, the thermoplastic composition is heated at a temperature of at least about 90° C., more specifically at least about 100° C., to convert the thermoplastic composition to a water stable composition. Typically, the thermoplastic composition will not be heated at a temperature over about 250° C., or over about 225° C. In some embodiments, the thermoplastic composition is heated at a temperature of at least about 115° C. to convert the thermoplastic composition to a water stable composition. In further embodiments, the thermoplastic composition is heated at a temperature of from about 130° C. to about 180° C. to convert the thermoplastic composition to a water stable composition. In some embodiments, the water content of the composition is reduced to a level below the level of bound water naturally present in the starch at ambient conditions. In other embodiments, the water content of the composition is reduced to 5% or less of the composition. In other embodiments, water content is about 4% or less. In another embodiment the water content is reduced to about 3% or less. In yet another embodiment, the water content is reduced to about 2% or less. Water content can be reduced by providing the starch composition at elevated temperatures under conditions wherein water can vaporize.

Although not required, the physical form of the thermoplastic polymer composition may be modified to provide a greater surface area to facilitate water removal from the compositions. The heating time necessary to convert a thermoplastic composition to a water stable form will depend, in general, on a variety of factors, including component compositions (i.e., particular starch, polyhydric alcohol and triglyceride and/or acid), heating temperature, physical form of the composition, and the like. Suitable times may range from instantaneously to about 24 hours, about 1 minute to about 24 hours, from about 5 minutes to about 12 hours, or from about 5 minutes to about 1 hour. In general, water content should not be reduced under conditions wherein decomposition, burning or scorching of the starch occurs, particularly in the case that visually noticeable or significant levels of decomposition, burning or scorching occurs.

In some embodiments, the thermoplastic compositions according to the present invention are formed by melt mixing and/or extruding a mixture comprising destructured starch, polyhydric alcohol, and triglyceride and/or acid, using conventional mixing and/or extrusion techniques. The mixture may be formed by combining destructured starch, polyhydric alcohol, and triglyceride and/or acid. Alternatively, the mixture may be provided by combining non-destructured starch, polyhydric alcohol, and triglyceride and/or acid, with the additional step of destructuring the starch in situ in the mixture, by any of the destructuring techniques discussed above. The components are typically mixed using conventional compounding techniques. The objective of the compounding step is to produce at least a visually homogeneous melt composition comprising the starch.

A suitable mixing device is a multiple mixing zone twin screw extruder with multiple injection points. The multiple injection points can be used to add the destructured starch, polyhydric alcohol and triglyceride and/or acid. A twin screw batch mixer or a single screw extrusion system can also be used. As long as sufficient mixing and heating occurs, the particular equipment used is not critical. An alternative method for compounding the materials comprises adding the starch, polyhydric alcohol, and triglyceride and/or acid to an extrusion system where they are mixed in progressively increasing temperatures. For example, a twin screw extruder with six heating zones may be employed. This procedure can result in minimal thermal degradation of the starch and may ensure that the starch is fully destructured. However, it may not be necessary to extrude a melt mixture, and, in general, any method known in the art or suitable for the purposes hereof can be used to combine the ingredients of the components to form the thermoplastic compositions of the present invention. Typically such techniques will include heat and mixing, and optionally pressure. The particular order or mixing, temperatures, mixing speeds or time, and equipment can be varied, as will be understood by those skilled in the art, however temperature should be controlled such that the starch does not significantly degrade. Further, if the temperature of the melt mixing and/or extrusion process is sufficiently high and for a sufficient time to eliminate at least a portion of bound water from the starch and drive a reaction between the polyhydric alcohol and the acid, the thermoplastic composition which is formed by melt extruding these components will convert to a water stable composition. For example, the melt extrusion can be conducted in an extruder provided with vents or other modifications which facilitate water removal and the conversion to a water stable composition. In such an embodiment, it is therefore advantageous to melt extrude the composition to a form which is suitable for end use, for example, as films, sheets, adhesives, binders, laminates, coatings, and foams; molded articles; and combinations thereof.

On the other hand, if the temperature or conditions at which the melt extrusion of the mixture comprising destructured starch, polyhydric alcohol and triglyceride and/or acid is conducted at a sufficiently low temperature and/or for an insufficient time to eliminate at least a portion of bound water from the starch and drive reaction between the polyhydric alcohol and the triglyceride and/or acid, the resulting extrudate comprises thermoplastic compositions of the invention, which may be further processed, if desired, and which are convertible to water stable compositions by further heating. The extrudate can therefore be provided in this embodiment in a form which facilitates handling, further processing, or the like. For example, a thermoplastic composition extrudate can be in pellet form, powder or crumb form or the like. In a specific embodiment, the thermoplastic composition extrudate is in a pellet form which is then suitable for melt extruding to a desired end use form. In this embodiment, the further melt extrusion of pellets (or extrudate of another form) to form films, sheets, adhesives, binders, laminates, coatings, and foams; molded articles, or other desired product forms, may be conducted under sufficient conditions of temperature and time to effect the conversion of the thermoplastic composition to a water stable composition or product. Alternatively, if the melt extrusion is not conducted under sufficient conditions of temperature and time to effect the conversion of the thermoplastic composition to a water stable composition, the resulting extrudate may be heated further to effect the conversion of the extruded thermoplastic composition to a water stable product.

In some embodiments, a thermoplastic composition in the form of pellets is formed by melt extruding destructured starch, polyhydric alcohol and triglyceride and/or acid. The extrusion process may not provide sufficient heating of the thermoplastic composition for a sufficient time to effect conversion to a water stable composition. The pellets are subsequently subjected to melt extrusion by conventional fiber spinning processes. The resulting fibers are rendered water stable by an additional heating step at a temperature of from about 100° C., more specifically 115° C., still more specifically from about 130° C., to about 180° C. Alternatively, the melt spinning process is conducted at a temperature in this range under conditions by which the resulting fibers are rendered water stable. In a further embodiment, the necessary water is eliminated from the fibers by flash evaporation as the fibers exit the spinneret swing to the reduction in pressure.

In some embodiments, it may be advantageous to provide the polyhydric alcohol and the triglyceride and/or acid as what is termed herein as a "pre-polymer". In these instances, the aforementioned transesterification reaction and/or ester condensation reaction has already at least partially, but not completely, taken place between the polyhydric alcohol and the triglyceride and/or acid before it is mixed with the starch. In further embodiments, the pre-polymer may also contain starch. Pre-polymers may take any suitable form which may be convenient to make, ship process and combinations thereof. Non-limiting examples of forms include strands, pellets, powder, and combinations thereof.

Methods

The water stability of compositions and articles comprising thermoplastic starch is measured in the following way. 1000 ml of tap water is charged to a clean glass beaker. A sample of the thermoplastic starch composition, or article comprising the thermoplastic starch composition, is placed in the water. The particular size of the test piece can vary depending on the type of article and method of construction, but in general the smallest dimension of the test piece should be smaller than 5 mm. Specific sizes for various forms are:

Sheet or Laminate: 5 cm×5 cm 0.5 mm—(no more than 0.5 mm thick)

Film, or Coating: 5 cm×5 cm×0.25 mm—(no more than 0.3 mm thick)

Molded Article: 2.5 cm×0.6 cm×0.7 mm—(no more than 1 mm thick)

Adhesive or binder: 5.0 cm×5.0 cm×0.5 mm—(no more than 1 mm thick)

Foam: 2.0 cm×2.0 cm×0.5 cm

A stir bar is added and the contents are stirred at least 30 rpm for 24 hours. After 24 hours the test piece is removed and dried at room temperature for 24 hours. The piece is measured again, and if the dimensions of the sheet change along any length by less than 10% then the piece and consequently the thermoplastic composition or article from which the test piece is made, is said to display water stability.

Plastic Articles

As used herein, "plastic article" is meant to encompass articles made solely from, or having at least one portion made from, thermoplastic compositions according to the present invention. Plastic articles include, but are not limited to extruded articles such as: films, sheets, adhesives, binders, laminates, coatings, and foams; molded articles; and combinations thereof. Personal hygiene articles and absorbent articles may be plastic articles or comprise plastic articles made from thermoplastic polymer compositions of the present invention.

Extruded Articles

Films

In some embodiments of the present invention, the plastic article is a film. As used herein, "film" means an extremely thin continuous piece of a substance having a high length to thickness ratio and a high width to thickness ratio, "high" meaning a ratio of over about 10:1. While there is no requirement for a precise upper limit of thickness, an upper limit would be about 0.254 mm, about 0.01 mm, or about 0.005 mm.

The films of the present invention can be employed in a variety of disposable products including, but not limited to, disposable personal hygiene articles (e.g., diapers, catamenials and the like), shrink-wrapping (e.g., food wraps, consumer product wraps, pallet and/or crate wraps, and the like), or bags (grocery bags, food storage bags, sandwich bags, resealable "Ziploc®"-type bags, garbage bags, and the like). The protective value of the present films, much like other films, may depend on its being continuous, i.e., without holes or cracks, such that it may serve as an efficient barrier to molecules such as atmospheric water vapor, and/or oxygen. In some embodiments of the present invention, the films are liquid impervious and suitable for use in absorbent disposable sanitary items including, but not limited to, disposable diapers, feminine hygiene pads and the like.

Films of the present invention may have a number of physical characteristics, such as biodegradability and compostability, for example. Films that perform well as compostable backsheets in personal hygiene articles including, but not limited to, diapers and feminine hygiene pads, may have characteristics such as those described in U.S. Pat. No. 5,498,692.

The films of the present invention may be made using any suitable process that is used for producing single or multi-layer films. Non-limiting examples of methods of use include cast film blowing, cast film extrusion and blown film extrusion. These methods as well as other suitable methods are described in U.S. Pat. No. 5,498,692.

In some embodiments, strands, pellets, or powders made from the presently disclosed thermoplastic polymer compositions, as well as combinations thereof, are dry blended and melt mixed in a film extruder. In embodiments in which insufficient mixing occurs in the film extruder, the strands, pellets, powders and combinations thereof, can be first dry blended and then melt mixed in a pre-compounding extruder followed by re-pelletization prior to film extrusion.

Sheets

In another embodiment of the present invention, the plastic article is a sheet. As used herein, "sheet" means a very thin continuous piece of a substance, having a high length to thickness ratio (over about 10:1) and a high width to thickness ratio (over about 10:1), wherein the material is thicker than about 0.254 mm. Sheeting may share many of the same characteristics as film in terms of properties and manufacture. However, sheeting may be stiffer than film, and may have a self-supporting nature. Differences in stiffness and support may arise as result of modification of the film manufacturing methods. Any suitable manufacturing method is of use. A non-limiting example of one method is cast extrusion. This method, as well as others, is described in U.S. Pat. No. 5,498,692.

Adhesives

In another embodiment of the present invention, the plastic article is an adhesive. As used herein "adhesive" means a material that joins two other materials, called adherends, together. A general discussion on adhesives can be found in the Encyclopedia of Polymer Science and Engineering, Vol. 1, pp. 547-577, (hereafter referred to as "EPSE-6"). In some embodiments of the present invention, the adhesive is applied as a liquid, optionally of a low viscosity. In the liquid form, the adhesive wets and flows into the crevices of the adherend. The liquid form of the adhesive is obtained by heating to the point that flow occurs, dissolving or dispersing the material in a solvent, or starting with liquid monomers or oligomers that polymerize or react after application. The adhesive then undergoes a phase change to a solid either by cooling, solvent evaporation, or reaction, in order for the joint to acquire the necessary strength to resist shearing forces. However, pressure-sensitive adhesives are an exception, since no phase change occurs.

The thermoplastic polymer compositions, or the starch compositions, of the present invention may be processed into a variety of adhesives, including but not limited to, hot melt, solution, dispersion and pressure sensitive adhesives.

As used herein, "hot-melt adhesive" refers to a thermoplastic polymer composition according to the present invention, which is heated to obtain a liquid of flowable viscosity, and after application to an adherend, cooled to obtain a solid. Generally, the molecular weight of the adhesive is tailored to provide flowability in the melt, but still be strong enough in the solid form to resist shearing forces experienced in the application. The primary feature of hot-melt adhesives is the ability of the thermoplastic material to flow above a certain temperature, high above the normal use temperature of the bond. Upon cooling, the material hardens, either by passing through the glass transition temperature of one of the components, or the crystallization temperature. This hardening lends physical integrity to the bond.

The adhesives of the present invention may be applied in any suitable way. Non-limiting examples of application include applying the adhesives as solutions, in water or an organic solvent, or in the form of aqueous dispersions. In either form, the solvent is removed after application for the adhesive to attain the required solid form. The solution or dispersion is usually applied to one of the surfaces to be bonded, and the solvent removed before the second surface is joined; often, heating is required to expedite the drying step. With porous substrates, such as paper or wood, final drying can take place after formation of the joint. Solids contents of the solutions vary from 5 to 95%, although values from 20 to 50% are most common.

As used herein, "dispersion" refers to adhesives prepared by true emulsion polymerization or dispersed as larger particles in some carrier fluid. In addition to their economic advantage, dispersions containing 40-50% solids offer lower viscosity than solutions, even if the solids are high molecular-weight polymers (EPSE-6). Adhesive dispersions of the present invention may be prepared by high shear in the presence of surfactants to obtain waterborne formulations, procedures which are well known to those skilled in the art.

Unlike the other adhesives disclosed herein, pressure sensitive adhesives comprising the thermoplastic polymers of the present invention, do not change their physical state from the initial application, to the final breaking of the adhesive bond. They remain permanently deformable, and may alter under even slight application of pressure. Pressure sensitive adhesives that are in dry form are permanently tacky at room temperature and firmly adhere to surfaces upon mere contact. The most common form of pressure-sensitive adhesive is on a backing, usually in tape form. Common masking tape, for example, is manually applied after the user removes the desired length from a roll. Many bandages are held to the skin by pressure-sensitive adhesives.

Binders

TPS materials can be used as adhesives or "binders" in any suitable applications, including but not limited to nonwoven materials, composites and the like. As used herein, a "binder" is an adhesive substance used in joining the fiber elements of a web in order to provide the fiber web cohesion integrity and or strength. In some embodiments comprising longer fiber nonwovens, the nonbonded material may be formed and then coated using the art recognized "dip" coating process, wherein the nonwoven is run through a bath of adhesive in a dispersion or solution, such as a colloidal dispersion in water. The adhesive then dries or sets and is optionally pressed to provide the bonded nonwoven. For materials lacking the mechanical integrity to withstand dip coating, spray coating may be used. Spray coating uses a sprayed adhesive including, but not limited to, a heated water dispersion of the adhesive, which then dries or cures and is optionally pressed to provide the bonded nonwoven.

For other materials which are made from fibers, the binding materials can be fibers themselves mixed within the web. These fibers can partially or completely melted and refused upon heating and cooling to provide cohesion of the web. The binder fibers can be made wholly of the binding material or just a part as in core shell arrangement in a fiber where the shell is the binder material.

Laminates

In some embodiments of the present invention, the aforementioned films and/or sheets are of use to laminate a substrate including, but not limited to, paper. The film and/or sheet may be all or part of a multilayer substrate, i.e., a laminate or composite. A laminate is defined as two or more substrates joined together. A laminate may have one or more layers comprising a blended starch composition as set forth herein. In another embodiment, a laminate may have a first layer comprising a thermoplastic starch composition as described herein and a second layer comprising a paper layer. In some embodiments, the laminate may also have a first layer comprising a polypropylene polymer, a second layer comprising a thermoplastic starch, and a third layer comprising polypropylene, or any combination of desired layers. As used herein, the terms first, second, or third layers are meant to describe separate layers and are not intended to be limiting as to the location of the layer. In one embodiment of the invention, a laminate has three layers wherein the outer two layers comprise a thermoplastic starch composition and the intermediate layer comprises a paper or paperboard material such as cardboard.

Coatings

As used herein, the term "coating" refers to both a layer exclusively on the surface of a substrate as well as a layer which to some degree penetrates the substrate. Suitable substrates include, but are not limited to, synthetic or bio sourced polymer film, paper, fabric, thread and yarn. Often the substrate will be paper. As used herein, "paper" refers to a substrate formed from cellulose fiber, including paper and cardboard. As used herein, "fabric" includes natural and synthetic fabrics. The fabrics may be knitted, woven or non-woven. Suitable fabrics include cotton, rayon, wool, and polyesters, as well as biodegradable fabrics. As used herein, "thread and yarn" include natural and synthetic threads and yarns, such as cotton, rayon, polyester, wool, silk, nylon, and acrylic as well as biodegradable threads. As used herein, "fiber" refers to a flexible, macroscopically homogeneous body having a high length-to-width ratio (over about 10:1) and a small cross section.

The coating may be applied to one or two sides of a substrate such as paper or fabric. Fabric and paper coated with the thermoplastic starch compositions of the present invention can be used to form items with improved water stability, such as wrapping paper, paper bags, plastic bags, cardboard containers, drink boxes, trays, table clothes, napkins.

The coatings may serve any suitable purpose including, but not limited to, use as barriers, decorative coatings, or for other purposes such as improving printing. Coatings may be used to apply adhesive for laminating one web to another or for manufacturing of pressure-sensitive tapes and labels. Coatings may also be used for saturation of a porous web substrate, such as paper, in order to improve its stability to moisture or to improve its strength.

The thickness of a coating is generally measured in "mils". One mil is equal to about 0.001 inch. The substrates generally have a coating up to about 5, from about 4 to about 0.5, or from about 2 to about 1, mils thick. Paper substrates generally have a coating with a thickness of from about 5 to about 0.5, or from about 2 to e.g., about 1, mils, while fabric substrates generally have a coating with a thickness of from about 5 to about 1, or from about 3 to about 2, mils. Thread and yarn substrates generally have a thinner coating than paper or fabric substrates, such as a thickness of from about 2 to about 0.2, or from about 1 to about 0.5, mils.

The coatings may comprise additives such as colorants. In some embodiments, such colorants are nonfugitive. As used herein, "nonfugitive" refers to an additive that does not escape from the TPS at a faster rate than which the material biodegrades. The coatings herein may be formed from a composition comprising the TPS and colorant. Alternatively, colors and designs may be printed on the items after manufacture. Preferably the colorants are non-toxic. Some items, such as garbage bags, may have coatings comprising deodorants, fragrances or disinfectants.

Coated articles may be formed using any conventional coating techniques or coating equipment. Coating techniques include, but are not limited to, extrusion coating, roller coating, brush coating, dip coating, spray coating, electrostatic coating, centrifugal coating and cast coating. Articles may be coated with melted TPS, and then exposed to a coolant, such as water or air. Substrates may be laminated with a sheet or film comprising TPS, such as a solution cast film or a melt pressed film. Slurries, or suspensions comprising TPS may be applied to a substrate, and the substrate then allowed to dry and, optionally, pressed.

Coatings applied in a non-solid form must be sufficiently fluid to be spread into a uniformly thin layer across the substrate. Therefore, coatings are typically applied as emulsions, as a hot melt (solid molten or softened by heat). Extrusion coating is similar to hot-melt coating. In extrusion coating, a film of molten polymer is deposited between two moving webs in a nip created by a rubber pressure roll and a chrome-plated steel chill roll.

Coatings may be applied to the web material wound in rolls, or to precut sheets. Items such as disposable plates and trays may be formed by pressing coated paperboard blanks between forming dies, as disclosed in U.S. Pat. No. 5,776,619.

Foams

In another embodiment of the present invention, the plastic article is foam. As used herein, "foam" refers the thermoplastic compositions of the present invention the apparent density of which has been substantially decreased by the presence of numerous cells distributed throughout its bulk (see ASTM D 883-62T, American Society for Testing and Materials, Philadelphia, Pa., (1962)). Such two-phase gas/solid systems in which the solid is continuous and composed of a synthetic polymer or rubber include cellular polymers (or copolymers), expanded plastics and foamed plastics (ENCYCLOPEDIA OF CHEMICAL TECHNOLOGY, Vol. 11, John Wiley & Sons, New York (1980)).

The gas phase may be distributed into pockets or voids called "cells" which are classified into two types, open and closed. Open-celled materials are foams the cells of which are inter-connected such that gases may pass freely through the cells. Closed-cell materials have cells that are discrete and isolated from each other.

Foams are further categorized into flexible and rigid foams. This classification is based on a particular ASTM test procedure (see ASTM D, Vol. 37, pp. 1566-1578, American Society of Testing and Materials, Philadelphia, Pa., (1978)). Flexible foam is foam which does not rupture when a 20×2.5×2.5 cm piece is wrapped around a 2.5 cm mandrel at a uniform rate of 1 lap/5 s at 15-25° C. Foams that do rupture under this test are referred to as rigid foams.

Foams according to the present invention may find any suitable used including, but not limited to, packaging, comfort cushioning, insulation, structural components and the like. In some areas of packaging, a foamed material having increased biodegradability and/or compostability would offer superior benefits to packaging that is currently used, such as polystyrene, paper and starch foams for example. In hot food containers, polystyrene offers significantly higher thermal insulation over the only currently degradable alternative, paper wraps. Foamed articles comprising the thermoplastic polymer compositions of the present invention have the thermal insulating properties of polystyrene, yet are biodegradable and/or compostable. These materials are ideal for hot food take-out and cold food packaging.

Foamed polystyrene chips are used as cushioned packing materials for consumer and industrial goods. Many of these chips are disposed of in landfills. Foamed chips comprising a thermoplastic polymer composition of the present invention can perform like polystyrene yet have increased biodegradability and/or compostability. Moreover, foamed chips according to the present invention may be water stable.

The foams of the present invention may be made using any suitable process. Non-limiting examples of methods are described in U.S. Pat. No. 5,498,692.

Molded Articles

In another embodiment of the present invention, the plastic article is a molded article. As used herein, "molded articles" refer to objects that are formed from thermoplastic materials. The thermoplastic materials may be, for example, injected, compressed, or blown by means of a gas into shape defined by a female mold. These objects can be solid objects like toys, or hollow like bottles and containers. Methods of making molded articles are described in further detail in U.S. Pat. No. 5,498,692.

Disposable Personal Care Products

The present invention further relates to disposable personal care products comprising thermoplastic polymer compositions of the present invention. In some embodiments, disposable personal care absorbent articles comprise a liquid pervious topsheet, a liquid impervious backsheet comprising a film of the present invention, and an absorbent core positioned between the topsheet and backsheet. In some embodiments, the personal care absorbent articles are compostable. Non-limiting examples of such absorbent articles include infant diapers, adult incontinent briefs and pads, and feminine hygiene pads and liners.

Additional personal care products comprising a thermoplastic polymer composition of the present invention include, but are not limited to: personal cleansing wipes; disposable health care products such as bandages, wound dressings, wound cleansing pads, surgical gowns, surgical covers, surgical pads; other institutional and health care disposables such as gowns, wipes, pads, bedding items such as sheets and pillowcases, foam mattress pads.

Films of the present invention that are used as liquid impervious backsheets in absorbent articles of the present invention, such as disposable diapers, typically have a thickness of from 0.01 mm to about 0.2 mm, or from 0.012 mm to about 0.051 mm.

In general, the liquid impervious backsheet is combined with a liquid pervious topsheet and an absorbent core positioned between the topsheet and the backsheet. Optionally, elastic members and tape tab fasteners can be included. While the topsheet, the backsheet, the absorbent core and elastic members may be assembled in a variety of well known configurations, a preferred diaper configuration is described generally in U.S. Pat. No. 3,860,003.

The topsheet may be soft-feeling, and non-irritating to the wearer's skin. Further, the topsheet may be liquid pervious, permitting liquids to readily penetrate through its thickness. A suitable topsheet may be manufactured from a wide range of materials including, but not limited to, porous foams, reticulated foams, apertured plastic films, natural fibers (e.g., wood or cotton fibers), synthetic fibers (e.g., polyester or polypropylene fibers) or from a combination of natural and synthetic fibers. In some embodiments, the topsheet is made of a hydrophobic material to isolate the wearer's skin from liquids in the absorbent core.

In one embodiment, the topsheet comprises staple-length fibers having a denier of about 1.5. As used herein, the term "staple-length fibers" refers to those fibers having a length of at least about 16 mm.

There are a number of manufacturing techniques which may be used to manufacture the topsheet. For example, the topsheet may be woven, non-woven, spunbonded, carded, and the like. In one embodiment, the topsheet is carded, and thermally bonded by means well known to those skilled in the fabrics art. The topsheet may have a weight from about 18 to about 25 g/m$^2$, a minimum dried tensile strength of at least about 400 g/cm in the machine direction, and a wet tensile strength of at least about 55 g/cm in the cross-machine direction. In some embodiments of the present invention, the top sheet comprises a thermoplastic polymer composition of the present invention.

The topsheet and the backsheet are joined together in any suitable manner. As used herein, the term "joined" encompasses configurations whereby the topsheet is directly joined to the backsheet by affixing the topsheet directly to the backsheet, and configurations whereby the topsheet is indirectly joined to the backsheet by affixing the topsheet to intermediate members which in turn are affixed to the backsheet. In one embodiment, the topsheet and the backsheet are affixed directly to each other in the diaper periphery by attachment means such as an adhesive or any other attachment means known in the art. For example, a uniform, continuous layer of adhesive, a patterned layer of adhesive, or an array of separate lines or spots of adhesive may be used to affix the topsheet to the backsheet. In some embodiments of the present invention, the adhesive comprises a thermoplastic polymer composition of the present invention.

Tape tab fasteners are typically applied to the back waistband region of the diaper to provide a fastening means for holding the diaper on the wearer. Any suitable tape tab fasteners are of use including, but not limited to those disclosed in U.S. Pat. No. 3,848,594. Tape tab fasteners or other diaper fastening means are typically applied near the corners of the diaper.

In some embodiments, diapers have elastic members disposed adjacent the periphery of the diaper. The elastic members may be located along each longitudinal edge so that they tend to draw and hold the diaper against the legs of the wearer. The elastic members may be secured to the diaper in an contractible condition so that in a normally unrestrained configuration the elastic members effectively contract or gather the diaper. The elastic members can be secured in a contractible condition in at least two ways. For example, the elastic members may be stretched and secured while the diaper is in an uncontracted condition. Alternatively, the diaper may be contracted, for example, by pleating, an elastic member secured and connected to the diaper while the elastic members are in their relaxed or unstretched condition.

The elastic members may take a multitude of configurations. For example, the width of the elastic members may be varied from about 0.25 mm to about 25 mm or more; the elastic members may comprise a single strand of elastic material or the elastic members may be rectangular or curvilinear. Still further, the elastic members may be affixed to the diaper in any of several ways which are known in the art. For example the elastic members may be ultrasonically bonded, heat and pressure sealed into the diaper using a variety of bonding patterns, the elastic members may simply be glued to the diaper and the like. In some embodiments of the present invention, the elastic members comprise a thermoplastic composition of the present invention.

The absorbent core of the diaper is positioned between the topsheet and backsheet. The absorbent core may be manufactured in a wide variety of sizes and shapes (e.g., rectangular, hour-glass, asymmetrical, etc.) and from a wide variety of materials. The total absorbent capacity of the absorbent core should, however, be compatible with the designed liquid loading for the intended use of the absorbent article or diaper. Further, the size and absorbent capacity of the absorbent core may vary to accommodate wearers ranging from infants through adults.

In some embodiments, the diaper has an hour-glass shaped absorbent core. The absorbent core is may be an absorbent member comprising a web or batt of airfelt, wood pulp fibers, and/or a particulate absorbent polymeric composition disposed therein.

In some embodiments, the absorbent polymeric composition of the absorbent core comprises a thermoplastic polymer composition of the present invention.

Other non-limiting examples of absorbent articles according to the present invention are sanitary napkins designed to receive and contain vaginal discharges such as menses. Disposable sanitary napkins are designed to be held adjacent to the human body through the agency of a garment, such as an undergarment or a panty or by a specially designed belt. Examples of the kinds of sanitary napkins to which the present invention is readily adapted are shown in U.S. Pat. Nos. 4,687,478 and in 4,589,876. It will be apparent that the films of the present invention comprising a thermoplastic polymer composition of the present invention described herein may be used as the liquid impervious backsheet of such sanitary napkins. On the other hand it will be understood the present invention is not limited to any specific sanitary napkin configuration or structure.

In general, sanitary napkins comprise a liquid impervious backsheet, a liquid pervious topsheet, and an absorbent core placed between the backsheet and the topsheet. The backsheet comprises a thermoplastic polymer composition of the present invention. The topsheet may comprise any of the topsheet materials discussed with respect to diapers. The adhesives used in may also comprise a thermoplastic polymer composition of the present invention. The absorbent core may comprise any of the absorbent core materials discussed with respect to diapers, including a thermoplastic polymer composition of the present invention.

Importantly, the absorbent articles according to the present invention may be biodegradable and/or compostable to a greater extent than conventional absorbent articles which employ materials such as a polyolefin (e.g., a polyethylene backsheet).

I. EXAMPLES

Example 1

A Single Layer Film

The following materials are mixed in a Haake Rheocord 90 melt mixer, Thermo Electron Corporation, Newington, N.H.:

30 g Ethylex™ 2015, hydroxyethylated starch (Tate and Lyle, Decatur, Ill.)

12.5 g Glycerol (Aldrich Chemicals, St. Louis, Mo.)

7.5 g Linseed oil (Aldrich Chemicals, St. Louis, Mo.)

0.0125 g p-Toluenesulfonic acid (Aldrich Chemicals, St. Louis, Mo.)

The starch and the glycerol are mixed for about 3 minutes at about 60 rpm at a temperature of about 160° C. The balance of components are added and mixed for an additional 7 minutes at about 60 rpm. The contents are removed and allowed to cool to room temperature. The mixture is then chopped using a knife into pieces approximately 50 mm in diameter.

After 24 hours, films of starch composition are made by melting the material between Teflon sheets in a Carver™ Press (Fred S. Carver Inc., Menomonee Falls, Wis.) at 165° C. Pressure on the sheets are adjusted to produce films of approximately 0.25 mm thick. The films are then identically cooled to room temperature by placing the molds between large (5 kg) aluminum plates and allowing the films to cool to room temperature.

One film is dried in a vacuum oven at 90° C. and 30 mm Hg for 12 hours. One film is dried in a convection oven at 115° C. for 12 hours. Another film simply allowed to cool for 12 hours at ambient air temperature (about 22° C.). The respective films are subjected to the water stability test as described herein. The films which were dried at elevated temperature (90° C. and 115° C.) do not dissolve or break-up, displaying water stability as defined herein. Films that are allowed simply to cool, without heat treatment, break up completely after 24 hours in water.

Example 2

Comparative Example

This example demonstrates a conventional process for melt mixing and creating films which are not water stable. The following materials are mixed in the described Haake Rheocord 90 melt mixer:

30 g Ethylex™ 2015 starch (Tate and Lyle, Decatur, Ill.)
12.5 g Glycerol (Aldrich Chemicals, St. Louis, Mo.)

The starch and the glycerol are mixed for about 3 minutes at about 60 rpm at a temperature of about 160° C. The balance of components are added and mixed for an additional 7 minutes at about 60 rpm. The contents are removed and allowed to cool to room temperature. The mixture is then chopped using a knife into pieces approximately 50 mm in diameter.

After 24 hours, films of starch composition are made by melting the material between Teflon sheets in a Carver™ Press (Fred S. Carver Inc., Menomonee Falls, Wis.) at 165° C. Pressure on the sheets are adjusted to produce films of approximately 0.25 mm thick. The films are then identically cooled to room temperature by placing the molds between large (5 kg) aluminum plates and allowing the films to cool to room temperature.

One film is dried in a vacuum oven at 90° C. and 30 mm Hg for 12 hours. One film is dried in a convection oven at 115° C. for 12 hours. Another film simply allowed to cool for 12 hours at ambient air temperature (about 22° C.). The respective films are subjected to the water stability test as described herein. In this case the films which were dried at elevated temperature (90° C. and 115° C.) and ambient temperature, break up completely after 24 hours in water and fail the water stability.

Example 3

Single Layer Film

This example demonstrates additional blending of TPS with water stability. The following materials are used:

6000 g Ethylex™ 2035 (Tate & Lyle, Decatur, Ill.)
2500 g Glycerol (Aldrich Chemicals, St. Louis, Mo.)
350 g Adipic acid (Solutia Chemicals, St. Louis, Mo.)
500 g Linseed oil (Aldrich Chemicals, St. Louis, Mo.)
2.5 g p-Toluenesulfonic acid (Aldrich Chemicals, St. Louis, Mo.)
500 g Polypropylene Profax™ PH835(Basell, Elkton, Md.)
500 g Maleated polypropylene G3003 (Eastman Chemicals, Kingsport, Tenn.)
50 g Magnesium stearate (Aldrich Chemicals, St. Louis, Mo.)

The starch, Linseed oil, p-Toluenesulfonic acid, polypropylene, maleated polypropylene and magnesium stearate (employed as a process aid) are mixed in a Henschel Raw Material Mixer (Green Bay, Wis.) for 4 minutes at 1000 rpm. The mixture is then fed into a B & P Process System Twin Screw Extrusion Compounding System (Saginaw, Mich.) with 40 mm co-rotating screws. Glycerol is fed through a liquid feed port at a rate that maintains the desired composition stated above. The screw speed is set at 90 rpm with the thermal profile as shown below:

|  | Temperature | | | | | | | | | |
|---|---|---|---|---|---|---|---|---|---|---|
|  | zone 1 | zone 2 | zone 3 | zone 4 | zone 5 | zone 6 | zone 7 | zone 8 | zone 9 | die |
| Set (° C.) | 85 | 85 | 100 | 145 | 155 | 160 | 160 | 160 | 140 | 100 |
| Actual (° C.) | 83 | 83 | 85 | 138 | 138 | 144 | 155 | 147 | 133 | 98 |

At these conditions the overall extrusion rate is 20 lbs/hour. A vacuum line is applied to two of three vent ports to extract water from the material during pelletization. Torque is 10%. The mixture is extruded into strands 0.3-0.8 cm in diameter and the strands are chopped to form pellets via a Conair pellitizer. The pellets are fed into a single screw extruder (Rheomix Model 202) with screw diameter of 0.75 inch. A constant taper screw having 20:1 length to diameter ratio and a 3:1 compression ratio is employed. The temperature of both heating zones of the extruder barrel is 160° C. The extruder is equipped with a die of width 6 inch and a die gap of 0.04 inch. The die is maintained at 100°. The screw rpm is kept constant at 30 rpm. The composition is forced through the die and is collected on a take-up roll collection system (Postex) at a rate that allows solidification of the Thermoplastic starch before take-up. The width of these films are nominally 4 inch and the thickness are approximately 0.002 inch.

After cooling to room temperature for 24 hours, 100 cm of film is dried in a vacuum oven at 90° C. and 30 mm Hg for 12 hours. Another 100 cm of film is dried in a convection oven at 115° C. for 12 hours. Another 100 cm of film is simply allowed to cool for 12 hours at ambient air temperature (about 22° C.). The respective films are subjected to the water stability test as described herein. The films which were dried at elevated temperature (90° C. and 115° C.) do not dissolve or break-up, displaying water stability as defined herein. Films that are allowed simply to cool, without heat treatment, break up completely after 24 hours in water.

Example 4

A Single Layer Film

The following materials are mixed in a Haake Rheocord 90 melt mixer, Thermo Electron Corporation, Newington, N.H.:

30 g Ethylex™ 2035 (Tate & Lyle, Decatur, Ill.)
12.5 g Glycerol (Aldrich Chemicals, St. Louis, Mo.)
5 g Soybean oil (Aldrich Chemicals, St. Louis, Mo.)
0.0125 g p-Toluenesulfonic acid (Aldrich Chemicals, St. Louis, Mo.)
2.5 g Polypropylene PH835 (Basell, Elkton, Md.))
2.5 g Maleated polypropylene G3003 (Eastman Chemicals, Kingsport, Tenn.)
0.25 g Magnesium stearate (Aldrich Chemicals, St. Louis, Mo.)

The starch and the glycerol are mixed for about 3 minutes at about 60 rpm at a temperature of about 165° C. The balance of components are added and mixed for an additional 7 minutes at about 60 rpm. The contents are removed and allowed to cool to room temperature. The mixture is then chopped using a knife into pieces approximately 50 mm in diameter.

After 24 hours, films of starch composition are made by melting the material between Teflon sheets in a Carver™ Press (Fred S. Carver Inc., Menomonee Falls, Wis.) at 165° C. Pressure on the sheets are adjusted to produce films of approximately 0.25 mm thick. The films are then identically cooled to room temperature by placing the molds between large (5 kg) aluminum plates and allowing the films to cool to room temperature.

One film is dried in a vacuum oven at 90° C. and 30 mm Hg for 12 hours. One film is dried in a convection oven at 115° C. for 12 hours. Another film simply allowed to cool for 12 hours at ambient air temperature (about 22° C.). The respective films are subjected to the water stability test as described herein. The films which were dried at elevated temperature (90° C. and 115° C.) do not dissolve or break-up, displaying water stability as defined herein. Films that are allowed simply to cool, without heat treatment, break up completely after 24 hours in water.

Example 5

A Single Layer Film

The following materials are mixed in a Haake Rheocord 90 melt mixer, Thermo Electron Corporation, Newington, N.H.:
30 g Ethylex™ 2035 (Tate & Lyle, Decatur, Ill.)
12.5 g Glycerol (Aldrich Chemicals, St. Louis, Mo.)
2.5 g Linseed oil (Aldrich Chemicals, St. Louis, Mo.)
0.0125 g p-Toluenesulfonic acid (Aldrich Chemicals, St. Louis, Mo.)
5.0 g Maleated polypropylene G3003 (Eastman Chemicals, Kingsport, Tenn.)
0.25 g Magnesium stearate (Aldrich Chemicals, St. Louis, Mo.)

The starch and the glycerol are mixed for about 3 minutes at about 60 rpm at a temperature of about 165° C. The balance of components are added and mixed for an additional 7 minutes at about 60 rpm. The contents are removed and allowed to cool to room temperature. The mixture is then chopped using a knife into pieces approximately 50 mm in diameter.

After 24 hours, films of starch composition are made by melting the material between Teflon sheets in a Carver™ Press (Fred S. Carver Inc., Menomonee Falls, Wis.) at 165° C. Pressure on the sheets are adjusted to produce films of approximately 0.25 mm thick. The films are then identically cooled to room temperature by placing the molds between large (5 kg) aluminum plates and allowing the films to cool to room temperature.

One film is dried in a vacuum oven at 90° C. and 30 mm Hg for 12 hours. One film is dried in a convection oven at 115° C. for 12 hours. Another film simply allowed to cool for 12 hours at ambient air temperature (about 22° C.). The respective films are subjected to the water stability test as described herein. The films which were dried at elevated temperature (90° C. and 115° C.) do not dissolve or break-up, displaying water stability as defined herein. Films that are allowed simply to cool, without heat treatment, break up completely after 24 hours in water.

Example 6

Multilayer Laminate Film

A sheet of thermoplastic starch film may be prepared as in Example 5 except for the final step of drying in a vacuum oven. The thermoplastic sheet may then be encased by a sheets of a polymer with better water barrier properties such as polypropylene. This may be the case when even greater water barrier properties are needed. The films are placed in Carver™ press stacked in the following order polypropylene (Basell Profax™ PH835), Thermoplastic starch, polypropylene. The material is then pressed at a temperature 160° C. After compression at 2000 lb for 10 min, the pressure is released and the film is allowed to cool to room temperature. The assembly is dried in a vacuum oven at 115° C. for 12 hours as in example 1.

Example 7

Disposable Diaper

A disposable baby diaper according to this invention is prepared as follows. The dimensions listed are for a diaper intended for use with a child in the 6-10 kilogram size range. These dimensions can be modified proportionately for different size children, or for adult incontinence briefs, according to standard practice.

1. Backsheet: 0.020-0.038 mm film consisting of a Thermoplastic starch (prepared as described in Example 3); width at top and bottom 33 cm; notched inwardly on both sides to a width-at-center of 28.5 cm; length 50.2 cm.

2. Topsheet: carded and thermally bonded staple-length polypropylene fibers (Hercules type 151 polypropylene); width at top and bottom 33 cm; notched inwardly on both sides to a width-at-center of 28.5 cm; length 50.2 cm.

3. Absorbent core: comprises 28.6 g of cellulose wood pulp and 4.9 g of absorbent gelling material particles (commercial polyacrylate from Nippon Shokubai); 8.4 mm thick, calendered; width at top and bottom 28.6 cm; notched inwardly at both sides to a width-at-center of 10.2 cm; length 44.5 cm.

4. Elastic leg bands: four individual rubber strips (2 per side); width 4.77 mm; length 370 mm; thickness 0.178 mm (all the foregoing dimensions being in the relaxed state).

The diaper is prepared in standard fashion by positioning the core material covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2 bands per side) of the core. The inner bands along each side are positioned ca. 55 mm from the narrowest width of the core (measured from the inner edge of the elastic bank). This provides a spacing element along each side of the diaper comprising the flexible topsheet/backsheet material between the inner elastic and the curved edge of the core. The inner bands are glued down along their length in the stretched state. The outer bands are positioned ca. 13 mm from the inner bands, and are glued down along their length in the stretched state. The topsheet/backsheet assembly is flexible, and the glued-down bands contract to elasticize the sides of the diaper.

Example 8

Lightweight Pantiliner

A lightweight pantiliner suitable for use between menstrual periods comprises a pad (surface area 117 cm$^2$; SSK air felt 3.0 g) containing 1.0 g of absorbent gelling material particles (commercial polyacrylate; Nippon Shokubai); said pad being interposed between a porous formed-film topsheet according to U.S. Pat. No. 4,463,045 and a backsheet which comprises a 0.03 mm thickness thermoplastic starch film, as prepared in accordance with Example 3.

Example 9

Sanitary Napkin

A catamenial product in the form of a sanitary napkin having two flaps extending outward from its absorbent core is prepared using a pad in the manner of Example 8 (surface area 117 cm²; 8.5 g SSK air felt), per the design of U.S. Pat. No. 4,687,478, Van Tillburg, Aug. 18, 1987. The backsheet and topsheet materials are the same as described in Example 8.

Example 10

Single Layer Film

This example demonstrates additional blending of TPS with water stability. The following materials are used:
6000 g Ethylex™ 2025 (Tate & Lyle, Decatur, Ill.)
2300 g Glycerol (Aldrich Chemicals, St. Louis, Mo.)
350 g Soybean oil (Aldrich Chemicals, St. Louis, Mo.)
2.3 g p-Toluenesulfonic acid (Aldrich Chemicals, St. Louis, Mo.)
500 g Polypropylene Profax™ PH 835 (Basell, Elkton, Md.)
500 g Maleated polypropylene G3003 (Eastman Chemicals, Kingsport, Tenn.)
50 g Magnesium stearate (Aldrich Chemicals, St. Louis, Mo.)

The starch, Soybean oil, p-Toluenesulfonic acid, polypropylene, maleated polypropylene and magnesium stearate (employed as a process aid) are mixed in a Henschel Raw Material Mixer (Green Bay, Wis.) for 4 minutes at 1000 rpm. The mixture is then fed into a B & P Process System Twin Screw Extrusion Compounding System (Saginaw, Mich.) with 40 mm co-rotating screws. Glycerol is fed through a liquid feed port at a rate that maintains the desired composition stated above. The screw speed is set at 90 rpm with the thermal profile as shown below:

| | Temperature | | | | | | | | | |
|---|---|---|---|---|---|---|---|---|---|---|
| | zone 1 | zone 2 | zone 3 | zone 4 | zone 5 | zone 6 | zone 7 | zone 8 | zone 9 | die |
| Set (° C.) | 85 | 85 | 100 | 145 | 155 | 160 | 160 | 160 | 140 | 100 |
| Actual (° C.) | 83 | 83 | 85 | 138 | 138 | 144 | 155 | 147 | 133 | 98 |

At these conditions the overall extrusion rate is 20 lbs/hour. A vacuum line is applied to two of three vent ports to extract water from the material during pelletization. Torque is 10%. The mixture is extruded into strands 0.3-0.8 cm in diameter and the strands are chopped to form pellets via a Conair pelletizer. The pellets are fed into a single screw extruder (Rheomix Model 202) with screw diameter of 0.75 inch. A constant taper screw having 20:1 length to diameter ratio and a 3:1 compression ratio is employed. The temperature of both heating zones of the extruder barrel is 160° C. The extruder is equipped with a die of width 6 inch and a die gap of 0.04 inch. The die is maintained at 100°. The screw rpm is kept constant at 30 rpm. The composition is forced through the die and is collected on a take-up roll collection system (Postex) at a rate that allows solidification of the Thermoplastic starch before take-up. The width of these films are nominally 4 inch and the thickness are approximately 0.002 inch.

After cooling to room temperature for 24 hours, 100 cm of film is dried in a vacuum oven at 90° C. and 30 mm Hg for 12 hours. Another 100 cm of film is dried in a convection oven at 115° C. for 12 hours. Another 100 cm of film is simply allowed to cool for 12 hours at ambient air temperature (about 22° C.). The respective films are subjected to the water stability test as described herein. The films which were dried at elevated temperature (90° C. and 115° C.) do not dissolve or break-up, displaying water stability as defined herein. Films that are allowed simply to cool, without heat treatment, break up completely after 24 hours in water.

Example 11

Disposable Diaper

The diaper of Example 7 is modified by replacing the backsheet with a backsheet consisting of a 0.020 to 0.038 mm thickness film comprising a starch thermoplastic film prepared as described in Example 10.

Example 12

Sheet

The film preparation procedure of Example 3 is modified by replacing the die on the extruder with a slot die of thickness approximately 0.25 cm and width 15 cm. Take-up after extrusion is accomplished by inserting the sheet emerging from the extruder between two counter-rotating cylinders. The sheet is drawn from the extruder in this manner and cut in lengths of 32 cm. Sheets of approximately 13 cm wide and 0.18 cm thick are obtained.

Example 13

Rigid Foam

A thermoplastic starch composition is prepared as in example 5, and 30 g of the thermoplastic starch composition and 0.3 g, Celogen® 125 FF (Chemtura Corporation, Middlebury, Conn.), a modified azodicarbonamide are charged to the mixing chamber of a Rheomix type 600 melt blender equipped with roller blades. The mixing chamber temperature is heated above the melting temperature of thermoplastic starch (165° C.), but below the degradation temperature of the blowing agent (195° C.). After mixing for 10 minutes at 60 rpm, the mixture is collected and is transferred to a heated aluminum pan, spread about so that the resulting mass is about 0.5 cm in thickness. The mixture is then place in an oven (National Appliance Company, model 5830) and heated to the TPS melt temperature again (165° C.), and is held at that temperature until the thermoplastic starch composition is completely molten (ca. 5 min). The oven temperature is then raised to 200° C. at which temperature the blowing agent degrades and thermoplastic composition begins foaming. At this point the thermoplastic starch foam is removed from the 200° C. oven. After cooling to room temperature the thermoplastic starch foam is placed in a oven at 115° C. for 12 hours.

Example 14

Molded Article

Injection molded articles are obtained by using a Mini Max Molder™ model CS-183 (Custom Scientific Instruments, Whippeny, N.J.). The temperature of the rotor and strator cup is held constant at 165° C. About 1.0 grams the thermoplastic starch pellets as described in example 10 is charged to the stator cup and allowed to melt for 3 minutes. The molten thermoplastic starch composition is radially mixed by raising and lowering the rotor tip five times. A dumbbell-shaped steel mold is sprayed with a light coating of mold silicone release agent. The mold is placed on the mold support wheel of the Mini Max Molder™ and the molten composition is injected into the mold by action of the rotor tip. The thermoplastic starch is molded into a dumbbell shaped pieces 0.03 inch thick, 1 inch long, 0.125 inch wide at the middle of the piece and 0.25 inch wide at the ends. These molded parts are suitable for mechanical testing. The test pieces are placed in a vacuum oven at 115° C. for 12 hours. They are then subjected to a water stability test where they are placed in 1000 ml of tap water for 24 hours, then removed from the water and allowed to dry for 24 hours. They experience less than 10% dimensional change from their pre-soak dimensions and are said to have passed the water stability test.

Example 15

Compostable Adhesive

Thermoplastic starch compositions described herein may be used as a hot-melt adhesive. A composition of thermoplastic starch is prepared as in example 10, except that instead of casting the pellets into a film, they will be used as an adhesive in the following manner. About 1 g of the thermoplastic starch is placed between two sheets of paper (Georgia Pacific Spectrum DP white). The assembly is placed in a Carver™ Press (Fred S. Carver Inc., Menomonee Falls, Wis.) and is then pressed at a temperature 165° C. After compression at 2000 lb force for 30 min, the pressure is released and the bonded assembly is allowed to cool to room temperature.

Example 16

Coating On Fabric

A film of is prepared as described in example 5 except for the final drying step in a vacuum oven. The Thermoplastic starch sheet is placed on top of a 5 inch square section of untreated cotton fabric. The assembly is placed between release paper (Idesco) and placed into a Carver™ Press preheated to 160° C. The fabric/TPS assembly is pressed for 20 seconds at 1000 lbs. The resulting coated fabric is then removed from the press and allowed to cool. The coated fabric is then placed in a vacuum oven and dried at 115° C. for 12 hours then removed and allowed to cool. The fabric is then subjected to the following test to check water stability. About 20 ml of tap water is placed on the thermoplastic coated side of the fabric and allowed to remain for 1 hour. The fabric is free of darkening that would indicate penetration of the water.

Example 17

Binder Fibers

This example demonstrates additional blending and spinning of binder fibers with water stability. The following materials are used:
6000 g Ethylex™ 2015 (Tate & Lyle, Decatur, Ill.)
2500 g Glycerol (Aldrich Chemicals, St. Louis, Mo.)
450 g Linseed oil (Aldrich Chemicals, St. Louis, Mo.)
2.5 g p-Toluenesulfonic acid (Aldrich Chemicals, St. Louis, Mo.)
500 g Maleated polypropylene (Eastman Chemicals, Kingsport, Tenn.)
50 g Magnesium stearate (Aldrich Chemicals, St. Louis, Mo.)

The starch, linseed oil, p-toluenesulfonic acid, maleated polypropylene and magnesium stearate are mixed in a Henschel Raw Material Mixer (Green Bay, Wis.) for 4 minutes at 1000 rpm. The mixture is then fed into a B & P Process System Twin Screw Extrusion Compounding System (Saginaw, Mich.) with 40 mm co-rotating screws. Glycerol is fed through a liquid feed port at a rate that maintains the desired composition (stated above). The screw speed is set at 90 rpm with the thermal profile as shown below:

| | Temperature | | | | | | | | | |
|---|---|---|---|---|---|---|---|---|---|---|
| | zone 1 | zone 2 | zone 3 | zone 4 | zone 5 | zone 6 | zone 7 | zone 8 | zone 9 | die |
| Set (° C.) | 85 | 85 | 100 | 145 | 155 | 160 | 160 | 160 | 140 | 100 |
| Actual (° C.) | 83 | 83 | 85 | 138 | 138 | 144 | 155 | 147 | 133 | 98 |

At these conditions the overall extrusion rate is 20 lbs/hour. A vacuum line is applied to two of three vent ports to extract water from the material during pelletization. Torque is 10%. The mixture is extruded into strands 0.3-0.8 cm in diameter and the strands are chopped to form pellets via a Conair pellitizer. The pellets are dried for 12 hours in a through air dryer at 150° F. The pellets are fed into a Hills 4-hole extruder test stand (Hills, Inc., West Melbourne, Fla.) with a Hills bicomponent sheath/core 4-hole spin pack. The equipment features two extruders that feed to a single spin head to produce bicomponent fibers. For single component fibers, both extruders are set to identical conditions as follows and the same material is fed into both extruders:

| | Extruder Melt Pressure (psi) | Barrel Zone 1 (° C.) | Barrel Zone 2 (° C.) | Barrel Zone 3 (° C.) | Extruder Pressure (psi) | Melt Pump Speed (rpm) | Spin Head (° C.) |
|---|---|---|---|---|---|---|---|
| Set Extruder 1 (° C.) | 1400 | 125 | 160 | 170 | 1500 | 464 | 165 |
| Set Extruder 2 (° C.) | 1400 | 125 | 160 | 170 | 1500 | 464 | |

Fibers are collected in on a screen through an attenuating air jet at a mass throughput of 0.8 g/hole-min. The air jet is set at 20 psi. The Thermoplastic starch fibers are collected, chopped with a knife to lengths approximately 2 cm. The starch fibers are mixed with unbonded staple polyester fibers (Wellman, Fort Mill, S.C.) at a ratio of 10:1 by weight polyester to starch web for a total basis weight of approximately 50 gsm. The unbonded web is placed in a Carver™ Press and pressed at 100 psi at 165° C. for 10 minutes between Teflon sheets. The web is removed and allowed to cool. The web is dried overnight in a vacuum oven at 115° C. The web is subjected to the following water stability test: A 5 cm×5 cm web is placed in 1000 ml of water and allowed to soak for 24 hours. The web is removed and if it remains intact, it is said to pass the water stability test. The dried web passes the water stability test.

Example 18

A Single Layer Film

The following materials are mixed in a Haake Rheocord 90 melt mixer, Thermo Electron Corporation, Newington, N.H.:
30 g Ethylex™ 2035 (Tate & Lyle, Decatur, Ill.)
12.5 g Glycerol (Aldrich Chemicals, St. Louis, Mo.)
2.5 g Adipic acid (Solutia Chemicals, St. Louis, Mo.)
2.5 g Soybean oil (Aldrich Chemicals, St. Louis, Mo.)
5.0 g Maleated polypropylene G3003 (Eastman Chemicals, Kingsport, Tenn.)
0.25 g Magnesium stearate (Aldrich Chemicals, St. Louis, Mo.)

The starch and the glycerol are mixed for about 3 minutes at about 60 rpm at a temperature of about 165° C. The balance of components are added and mixed for an additional 7 minutes at about 60 rpm. The contents are removed and allowed to cool to room temperature. The mixture is then chopped using a knife into pieces approximately 50 mm in diameter.

After 24 hours, films of starch composition are made by melting the material between Teflon sheets in a Carver™ Press (Fred S. Carver Inc., Menomonee Falls, Wis.) at 165° C. Pressure on the sheets are adjusted to produce films of approximately 0.25 mm thick. The films are then identically cooled to room temperature by placing the molds between large (5 kg) aluminum plates and allowing the films to cool to room temperature.

One film is dried in a vacuum oven at 90° C. and 30 mm Hg for 12 hours. One film is dried in a convection oven at 115° C. for 12 hours. Another film simply allowed to cool for 12 hours at ambient air temperature (about 22° C.). The respective films are subjected to the water stability test as described herein. The films which were dried at elevated temperature (90° C. and 115° C.) do not dissolve or break-up, displaying water stability as defined herein. Films that are allowed simply to cool, without heat treatment, break up completely after 24 hours in water.

Example 19

A Single Layer Film

The following materials are mixed in a Haake Rheocord 90 melt mixer, Thermo Electron Corporation, Newington, N.H.:
30 g Ethylex™ 2035 (Tate & Lyle, Decatur, Ill.)
12.5 g Glycerol (Aldrich Chemicals, St. Louis, Mo.)
2.5 g Adipic acid (Solutia Chemicals, St. Louis, Mo.)
2.5 g Linseed oil (Aldrich Chemicals, St. Louis, Mo.)
5.0 g Maleated polypropylene G3003 (Eastman Chemicals, Kingsport, Tenn.)
0.25 g Magnesium stearate (Aldrich Chemicals, St. Louis, Mo.)

The starch and the glycerol are mixed for about 3 minutes at about 60 rpm at a temperature of about 165° C. The balance of components are added and mixed for an additional 7 minutes at about 60 rpm. The contents are removed and allowed to cool to room temperature. The mixture is then chopped using a knife into pieces approximately 50 mm in diameter.

After 24 hours, films of starch composition are made by melting the material between Teflon sheets in a Carver™ Press (Fred S. Carver Inc., Menomonee Falls, Wis.) at 165° C. Pressure on the sheets are adjusted to produce films of approximately 0.25 mm thick. The films are then identically cooled to room temperature by placing the molds between large (5 kg) aluminum plates and allowing the films to cool to room temperature.

One film is dried in a vacuum oven at 90° C. and 30 mm Hg for 12 hours. One film is dried in a convection oven at 115° C. for 12 hours. Another film simply allowed to cool for 12 hours at ambient air temperature (about 22° C.). The respective films are subjected to the water stability test as described herein. The films which were dried at elevated temperature (90° C. and 115° C.) do not dissolve or break-up, displaying water stability as defined herein. Films that are allowed simply to cool, without heat treatment, break up completely after 24 hours in water.

Example 20

A Single Layer Film

The following materials are mixed in a Haake Rheocord 90 melt mixer, Thermo Electron Corporation, Newington, N.H.:
30 g Ethylex™ 2035 (Tate & Lyle, Decatur, Ill.)
12.5 g Glycerol (Aldrich Chemicals, St. Louis, Mo.)
2.5 g Linseed oil (Aldrich Chemicals, St. Louis, Mo.)
2.5 g Soybean oil (Aldrich Chemicals, St. Louis, Mo.)
5.0 g Maleated polypropylene G3003 (Eastman Chemicals, Kingsport, Tenn.)
0.125 g p-Toluenesulfonic acid (Aldrich Chemicals, St. Louis, Mo.)
0.25 g Magnesium stearate (Aldrich Chemicals, St. Louis, Mo.)

The starch and the glycerol are mixed for about 3 minutes at about 60 rpm at a temperature of about 165° C. The balance of components are added and mixed for an additional 7 minutes at about 60 rpm. The contents are removed and allowed to cool to room temperature. The mixture is then chopped using a knife into pieces approximately 50 mm in diameter.

After 24 hours, films of starch composition are made by melting the material between Teflon sheets in a Carver™ Press (Fred S. Carver Inc., Menomonee Falls, Wis.) at 165° C. Pressure on the sheets are adjusted to produce films of approximately 0.25 mm thick. The films are then identically cooled to room temperature by placing the molds between large (5 kg) aluminum plates and allowing the films to cool to room temperature.

One film is dried in a vacuum oven at 90° C. and 30 mm Hg for 12 hours. One film is dried in a convection oven at 115° C. for 12 hours. Another film simply allowed to cool for 12 hours at ambient air temperature (about 22° C.). The respective films are subjected to the water stability test as described herein. The films which were dried at elevated temperature (90° C. and 115° C.) do not dissolve or break-up, displaying water stability as defined herein. Films that are allowed simply to cool, without heat treatment, break up completely after 24 hours in water.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A thermoplastic polymer composition comprising:
a water stabilized blend of
  a. from about 50% to about 85% of thermoplastic destructured starch; and
  b. from about 5% to about 50% of transesterification products;
  wherein a polyhydric alcohol initially plasticizes a destructured starch to make said thermoplastic destructured starch; and
  wherein said transesterification products are formed in situ in the presence of said thermoplastic destructured starch from a chemical reaction in a reactant mixture consisting essentially of:
    i. polyhydric alcohol having alcohol functional groups; and
    ii. triglyceride having ester functional groups;
  said functional groups being present in said reactant mixture in a molar ratio of alcohol functional groups to ester functional groups of from about 1:1 to about 200:1;
wherein the starch and the reactant mixture are heated during said chemical reaction at a sufficient temperature and time to eliminate at least a portion of bound water from the starch and drive the chemical reaction between the polyhydric alcohol and the triglyceride to a point to effect the water stability of the thermoplastic polymer composition; and
whereby the amount of polyhydric alcohol is reduced to effect water stability of the thermoplastic polymer composition.

2. The thermoplastic polymer composition of claim 1, wherein said triglyceride is present in oil selected from the group consisting of: coconut oil; corn germ oil; olive oil; palm seed oil; cottonseed oil; palm oil; rapeseed oil; sunflower oil; whale oil; soybean oil, peanut oil, linseed oil, tall oil, and combinations thereof.

3. The thermoplastic polymer composition of claim 1, wherein said polyhydric alcohol is selected from the group consisting of: glycerol; glycol; sugar; sugar alcohol; and combinations thereof.

4. The thermoplastic polymer composition of claim 1, wherein said polymer composition is blended with additional polymer.

5. The thermoplastic polymer composition of claim 4, wherein said additional polymer is selected from the group consisting of: polyhydroxyalkanoate; polyvinyl alcohol; polyethylene; polypropylene; polyethylene terephthalate; maleated polyethylene; maleated polypropylene; polylactic acid; modified polypropylene; nylon; caprolactone; and combinations thereof.

6. The thermoplastic polymer composition of claim 1, wherein said composition is combined with filler to form a composite.

7. The thermoplastic polymer composition of claim 6, wherein said filler is selected from the group consisting of: talc; clay; pulp; flour; walnut shells; cellulose; cotton; jute; raffia; rice chaff; animal bristles; chitin; granular starch; diatomaceous earth; nanoparticles; carbon fibers; kenaf; and combinations thereof.

8. A plastic article comprising the thermoplastic polymer composition according to claim 1.

9. The plastic article of claim 8, wherein said article is a molded article, extruded article, and combinations thereof.

10. The plastic article of claim 9, wherein said article is selected from the group consisting of: sheets; films; adhesives; binders; laminates; coatings; foams; and combinations thereof.

11. The thermoplastic polymer composition of claim 1, wherein said composition is biodegradable.

12. The thermoplastic polymer composition of claim 11, wherein said blend further comprises polymers selected from the group consisting of: polyvinyl alcohol; ester polycondensates; aliphatic/aromatic polyesters; and combinations thereof.

13. The thermoplastic polymer composition of claim 12, wherein said polymers are selected from the group consisting of: polybutylene succinate; polybutylene succinate co-adipate; co-polyesters of butylene diol, adipic acid, terephtalic acid, and combinations thereof; and combinations thereof.

14. A personal hygiene article comprising the thermoplastic polymer composition according to claim 1.

15. An absorbent article comprising the thermoplastic polymer composition according to claim 1.

16. Packaging comprising the thermoplastic polymer composition according to claim 1.

17. A starch composition comprising a composition mixture of:
  a. from about 50% to about 85% of the composition mixture being starch selected from the group consisting of native starch, destructured starch, and combinations thereof;
  b. from about 11 to about 50% of the composition mixture being transesterification products formed in situ from a reactant mixture consisting essentially of about 10% to about 30% of the composition mixture being polyhydric alcohol and from about 1% to about 20% of the composition mixture being triglyceride;
  wherein the starch and the reactant mixture are heated during said chemical reaction at a sufficient temperature and time to eliminate at least a portion of bound water from the starch and drive the chemical reaction between the polyhydric alcohol and the triglyceride to a point to effect water stability of the thermoplastic polymer composition; and
  whereby the amount of polyhydric alcohol is reduced to effect water stability of the thermoplastic starch composition.

18. The thermoplastic starch composition of claim 17, wherein said starch is destructured starch.

* * * * *